United States Patent [19]
Parsons

[11] 3,995,644
[45] Dec. 7, 1976

[54] PERCUTANEOUS CONNECTOR DEVICE
[75] Inventor: Walter E. Parsons, Kissimmee, Fla.
[73] Assignee: The United States of America as represented by the Administrator of the National Aeronautics and Space Administration, Washington, D.C.
[22] Filed: Sept. 16, 1975
[21] Appl. No.: 613,734

[52] U.S. Cl. .................................. 128/418; 3/1.1; 339/252 R
[51] Int. Cl.² ......................................... A61N 1/36
[58] Field of Search ........... 128/2.1 E, 2.06 R, 418, 128/404, 419 P, DIG. 4; 3/1.1, 1; 339/252 R, 252 P, 252 T

[56] References Cited
UNITED STATES PATENTS

| 2,719,956 | 10/1955 | Leighton | 339/252 T |
| 3,336,919 | 8/1967 | Russ | 128/2.1 E |
| 3,722,005 | 3/1973 | Cowland | 128/2.1 E |
| 3,862,633 | 1/1975 | Allison et al. | 128/2.06 E |

FOREIGN PATENTS OR APPLICATIONS

| 43,465 | 3/1934 | France | 339/252 P |
| 24,394 | 12/1904 | United Kingdom | 339/252 R |
| 708,468 | 5/1954 | United Kingdom | 339/252 P |

OTHER PUBLICATIONS
Kadefors et al., "A Percutaneous Electrode . . . Humans", Med. & Biol. Eng., vol. 8, pp. 129–135, 1970.

Primary Examiner—Robert W. Michell
Assistant Examiner—Lee S. Cohen
Attorney, Agent, or Firm—James O. Harrell; Gary F. Grafel; John R. Manning

[57] ABSTRACT

A percutaneous connector device for facilitating the passage of electrical signals from an external source through the skin of a patient to internal portions of the body such as muscles and nerves. The connector device includes a bio-compatible shell having an enlarged disk shaped portion for being implanted below the skin of the patient. The shell has a first and second electrically conductive post carried therein upon which a plug can be readily connected and disconnected therefrom. A modified form of the invention utilizes a unipolar connector that is adapted to be plugged into a shell implanted below the skin of a patient. Both of the connector devices are designed so as to be separated when a predetermined force is applied thereto in order to prevent excessive force from being applied to the implanted bio-compatible shell.

1 Claim, 8 Drawing Figures

PERCUTANEOUS CONNECTOR DEVICE

ORIGIN OF THE INVENTION

The invention described herein was made by an employee of the United States Government and may be manufactured and used by or for the Government for governmental purposes without the payment of any royalties thereon or therefor.

BACKGROUND OF THE INVENTION

This invention relates generally to a percutaneous connector and more particlarly to a connector which includes a bio-compatible shell that is implanted under the skin of a patient.

The medical community has long been aware that movement could be induced in living muscle fibers by electrical impulses. Further, tiny platinum wires, attached to small pads on selective nerves, can be brought through the surface of the skin and attached to external power supplies to move the associated muscles. By selection of the proper type of electrical stimulation, the muscle movement is predictable and repeatable. However, since the epithelial layer of skin will not form a union with the platinum wires which will resist the entry of bacteria, the direct application of this knowledge had to wait for the development of material suitable for a permanent percutaneous implant.

Various percutaneous conduit devices such as disclosed in U.S. Pat. No. 3,633,965 have been developed for facilitating the passages of wires and the like through the skin without rejection. One suitable conduit device is constructed of vitreous carbon.

While the problem of rejection has been minimized, there still remains the problem of implanting a shell which is bio-compatible with the skin so that such can remain permanently in the patient's body and connections can be readily made thereto. Permanent connections are not suitable in that if the lead feeding thereto is accidentally pulled, such could possibly dislodge the implanted shell.

SUMMARY OF THE INVENTION

The invention relates to a percutaneous connector device for facilitating the passage of electrical signals from an external source through the skin of a patient to an internal portion of the body, such as muscles and the like. The connector includes a shell having an enlarged disk shaped base portion for being implanted below the skin of the patient. A cylindrical portion is integral with the base portion and extends outwardly therefrom for passing through the skin of the patient. A tubular bore is exposed in the cylindrical portion. A first electrical conductive post is carried within the tubular bore and has an enlarged head extending outwardly beyond the shell with a circumferential groove provided therein. A second electrical conductive post is coaxially disposed on the first conductive post and is electrically insulated therefrom. The second conductive post has an enlarged head extending outwardly beyond the shell with a circumferential groove provided therein.

A plug means including a non-conductive body is provided for being attached to the shell. The plug means includes a first horseshoe shaped electrode carried by the non-conductive body with an open end portion of the horseshoe shaped electrode terminating adjacent an open end of a slot provided in a body portion of the plug. A second horseshoe shaped electrode is carried by the non-conductive body in spaced relation from the first electrode with an open end portion thereof terminating adjacent an open end of the slotted opening. Means is provided for coupling the electrical signals from the external source to the first and second horseshoe shaped electrodes of the plug means. The first and second horseshoe shaped electrodes are resiliently biased for snapping in the grooves of the first and second electrically conductive post for providing electrical connection between the plug means and the shell. The tension in the first and second horseshoe shaped electrodes is preset such that the plug means may readily be connected and disconnected from the conductive posts without damaging the tissue securing the implanted shell within the patient.

A modified form of the invention includes a bio-compatible shell constructed of electrically conductive material having an enlarged disk shaped portion for being implanted below the skin of the patient. The cylindrical portion is integral with the base portion and extends outwardly therefrom for passing through the skin of the patient. A circular socket or cavity is provided in and defined by an inner wall of the cylindrical portion. The cavity has a larger diameter adjacent the base portion than adjacent the outer end of the cylindrical portion. A unipolar plug is adapted to be inserted within the cavity for making electrical connection therebetween. The plug means includes a base portion having a post extending outwardly therefrom. Radially extending electrodes are carried by the post for making electrical contact with the shell when inserted within the cavity of the shell. Means is provided for coupling electrical signals from an external source to the radially extending electrodes of the plug means. The electrodes are resiliently biased outwardly for engaging the wall of the cavity of the shell producing a predetermined locking force between the shell and the plug means when the plug means is inserted therein.

Accordingly, it is the general object of the present invention to provide an improved percutaneous connector that can be separated with a predetermined force.

Another object of the present invention is to provide a percutaneous connector that is bio-compatible with the body so as not to invoke rejection but permits a union with the skin sufficient to resist the entrance of bacteria into the body.

Still another important object of the present invention is to provide a percutaneous connector that can be readily implanted in a patient's body.

These and other objects and advantages of the invention will become apparent upon reference to the following specification, attendant claims and drawings.

DESCRIPTION OF A PREFERRED EMBODIMENT

Figure 1:
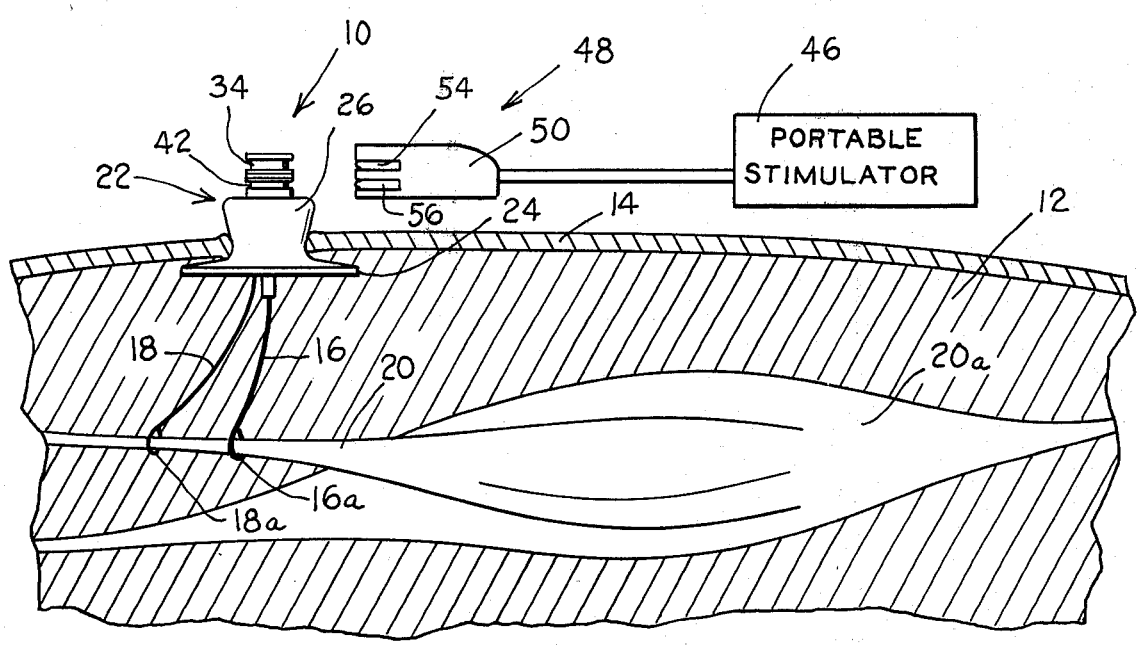
FIG. 1 is a side elevational view illustrating a percutaneous connector implanted within a patient's limb, such as a leg, with electrodes coupled to muscles extending therethrough.
Figure 2:
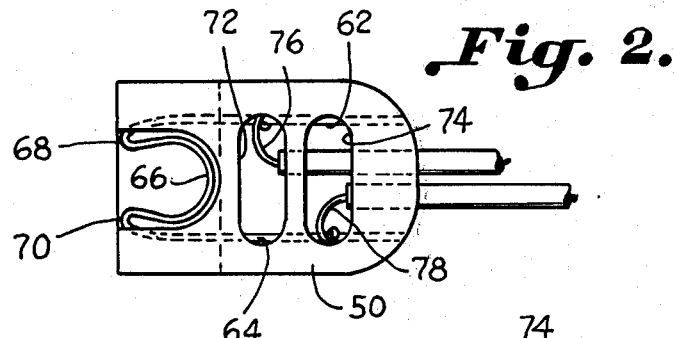
FIG. 2 is an enlarged, plan view of a plug forming part of the subject invention.

Referring in more detail to FIGS. 1 through 4 of the drawings, there is illustrated a percutaneous connector generally designated by the reference character 10 implanted in a limb 12 of a patient extending through the outer layer of skin 14. Electrodes 16 and 18 extend downwardly from the connector and are wrapped around a nerve 20 connected to a muscle 20a extending through the patient's limb. These electrodes 16 and 18 may be constructed of any suitable material and in one particular instance, are constructed of platinum with the looped end portion 18a and 16a being in the form of a pad with the platinum wire extending through the center thereof for contacting the nerve 20. Insulating tubes are carried on the electrodes 16 and 18 and can be constructed of any suitable material such as conventional implantable silastic or polytetrafluroethylene (teflon) tubing.

Figure 4:
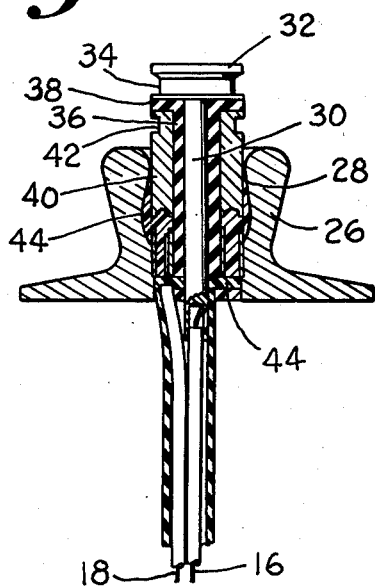
FIG. 4 is a cross-sectional view of an implanted biocompatible shell such as shown in FIG. 1.
Figure 3:
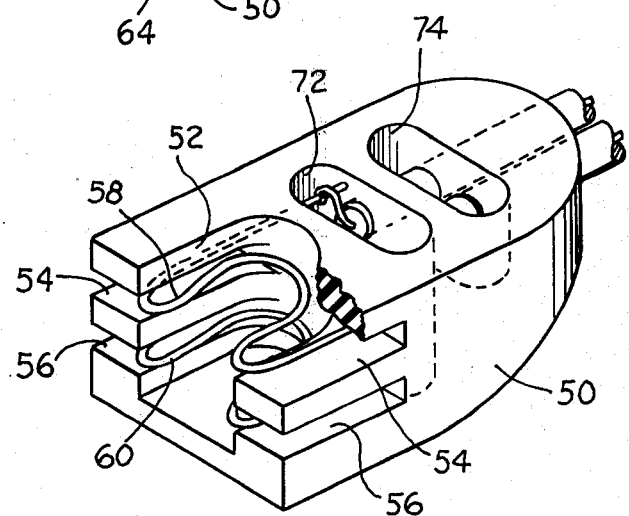
FIG. 3 is an enlarged, perspective view of the plug illustrated in FIG. 2.

The connector includes a shell generally designated by the reference character 22 constructed of biocompatible material such as vitreous carbon. The shell includes an enlarged disk shaped base portion 24 which is surgically implanted below the skin layer 14. Extending upwardly and integral with the base portion 24 is a cylindrical portion 26 which extends outwardly beyond the skin layer 14. An intermediate portion of the cylindrical portion 26 has a reduced radius which the skin layer 14 abuts against upon healing to produce a seal therebetween in order to prevent the entrance of bacteria. The shell 22 as shown in FIG. 4 has a tubular bore 28 extending therethrough. A first electrical conductive post 30 having an enlarged head 32 is carried within the bore 28 with a shank portion extending coaxially within the bore 28. A circumferential groove 34 is provided in the enlarged head 32 of the first conductive post. A sleeve of insulation 36 is carried on the shank portion of the first conductive post 30 and has a circular flange portion 38 adjacent the top thereof which abuts against the enlarged head 32 of the first conductive post 30. A second electrically conductive post 40 is coaxially disposed on the insulation 36 so as to be electrically insulated from the first conductive post 30. The second electrically conductive post 40 also has a head with a circumferential groove 42 provided therein.

The first and second post 30 and 40 may be secured within the bore 28 by applying an epoxy glue 44 within the cylindrical portion 26 and adjacent the lower end of the shell 22. In one particular embodiment, the posts 30 and 40 are constructed of stainless steel whereas the insulation 36 is in the form of a nylon sleeve, or biocompatible insulating epoxy material.

The electrodes 16 and 18 may be connected to the electrically conductive posts 30 and 40 in any suitable manner. In one particular instance, a platinum extension is brazed to the bottom of the posts 30 and 40 and the electrodes 16 and 18 are connected to the platinum extension posts with conductive epoxy or crimped.

In order to connect signals produced by a signal generator 46 through the conductive posts 30 and 40 to the electrodes 16 and 18, a plug generally designated by the reference character 48 is utilized. This plug 48 includes an elongated main body portion constructed of any suitable material such as phenolic. Positioned adjacent to one end of the main body portion 50 is an open ended slot 52. Adjacent in the legs defining the open ended slot 52 are vertically spaced slots 54 and 56. The slots 54 and 56 are carried on opposite sides of the open ended slot 52. Carried within the slots 54 and 56 are first and second horseshoe shaped electrodes 58 and 60 respectively. The horseshoe electrodes are constructed of spring tempered beryllium copper wire which is gold plated. The electrodes 58 and 60 include elongated arms 62 and 64 which extend through slots provided in the main body 50 of the plug. The inner end of the elongated arms 62 and 64 are integral with an arcuate intermediate portion 66 which is in the form of a horseshoe shape. In one particular embodiment, the intermediate portion 66 is bent on a 0.05 inch radius with the loop portions 68 and 70 being spaced apart 0.08 inches.

The main body portion 50 has elliptical slots 72 and 74 provided therein so as to permit wires 76 and 78 to be secured to the arms of electrodes 58 and 60 respectively. The wire 76 can be secured to the arm 62 of the electrode 58 by any suitable means such as soldering. Similarly, the wire 78 is secured to the arm 64 of the electrode 60. After the wires 76 and 78 have been secured to the electrodes 58 and 60, the slots 72 and 74 are filled with a non-conductive epoxy cement. The wires 76 and 78 are, in turn, connected to the signal generator 46.

Since the distance between the looped ends 68 and 70 of the electrodes 58 and 60 is less than the diameter of the intermediate portion 66, such permits a snap connection when the electrodes 58 and 60 are fitted within grooves 34 and 42 of the posts 30 and 40. In one particlar embodiment, it is desired that the force required for snapping the plug 48 onto the post and disconnecting such therefrom be between 6 and 8 ounces. Such can vary according to the particular application of the device. It is important to maintain the disconnection force within certain limits so as to not damage the skin 14 when disconnecting the plug 48.

In operation, if it is desired to exercise the legs of a person who is paralyzed, first the socket 26 would be implanted within the leg and the electrodes 18 and 16 wrapped around the motor nerve 20 within the leg. The skin 14 heals around the cylindrical portion 26 of the shell 22. At predetermined intervals, the plug 46 would be snapped onto the posts 30 and 40 of the shell 22 so as to supply electrical pulses to the nerve 20. When the pulses are applied for stimulating the nerves and muscles, such causes movement within the leg which would minimize calcium buildup in the joints of the patient. The program of the electrical pulses supplied by the generator 46 would be varied for the particular application of the device.

Figure 5:
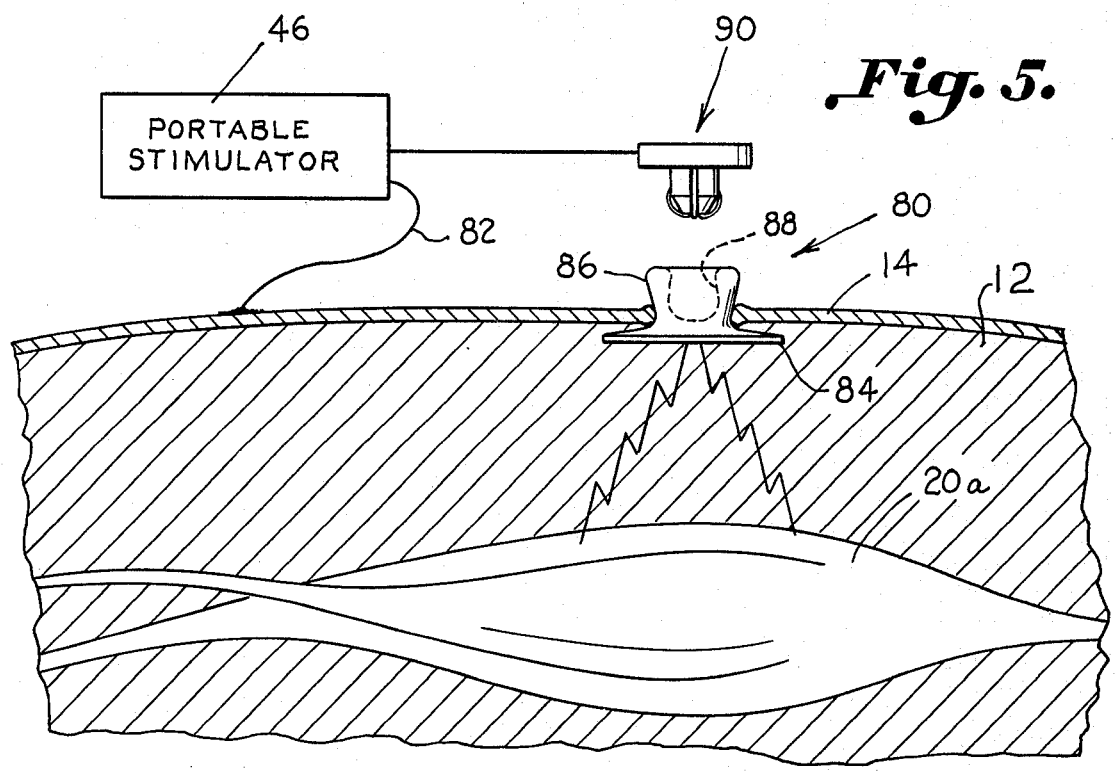
FIG. 5 is a side, elevational view illustrating a modified form of the invention wherein a unipolar percutaneous connector is implanted within a patient's limb such as a leg.
Figure 6:
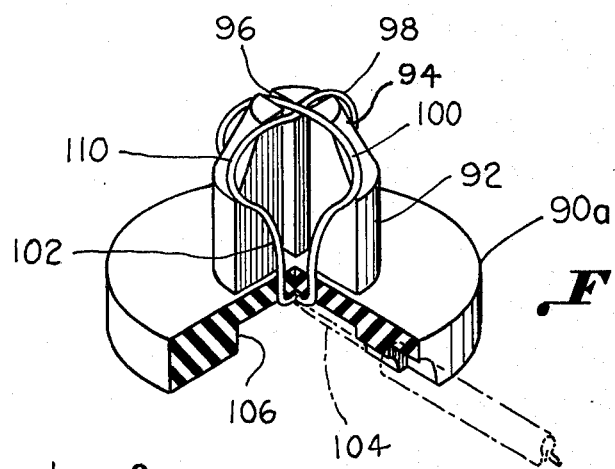
FIG. 6, is an enlarged, perspective view partially in such illustrating a plug means utilized with the device of FIG. 5.
Figure 7:
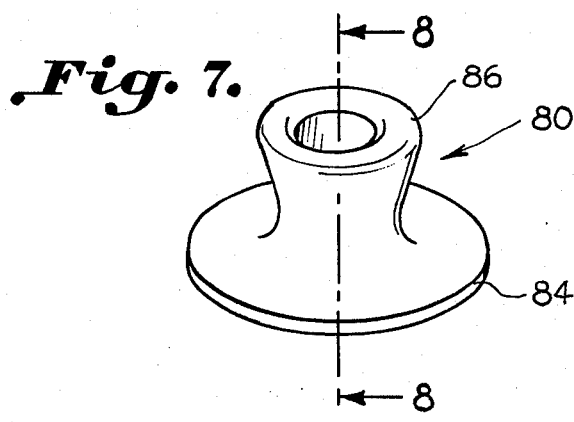
FIG. 7 is an enlarged, perspective view of an implanted bio-compatible shell forming part of the modified connector illustrated in FIG. 5.
Figure 8:
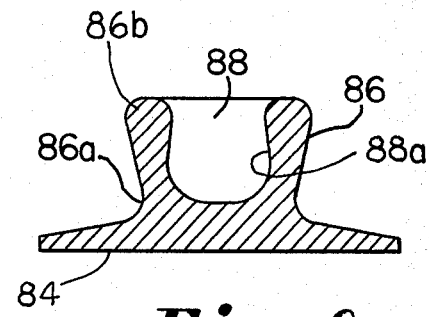
FIG. 8 is a sectional view taken along line 8—8 of FIG. 7.

A modified form of the invention is illustrated in FIG. 5 wherein a unipolar connector generally designated by that reference character 80 is implanted below the skin of a patient's limb and signals are transmitted through the flesh to the muscle 20a that is to be stimulated. A second electrode 82 extends from the portable stimulator 46 and is brought in contact with the skin 14. The connector device includes a shell constructed of an electrically conductive material such as a bio-compatible vitreous carbon material or of a titanium or other suitable material coated or deposited with bio-compatible carbon. The shell includes a disk shaped base portion 84 which is implanted below the skin of the patient. A cylindrical portion 86 has a first end portion 86a integral with the disk shaped base portion 84 and a second end portion 86b extending outwardly therefrom for passing through the skin of the patient. A circular socket or cavity 88 with a predetermined depth is provided in the second end portion 86b of cylindrical portion 86 to form an inner circular wall 88a having a diameter adjacent the first end portion 86b larger than the diameter adjacent the upper end thereof. In some applications, it is desirable to coat the inner circular wall 88a with a thin layer of highly conductive material such as gold so as to enhance the electrical coupling.

A plug means generally designated by the reference character 90 is provided for being inserted within the socket 88 of the shell 80. The plug means 90 includes a disk shaped base portion 90a that may be constructed of any suitable material such as brass. Extending upwardly from the base portion 90 is a post 92 that has a reduced upper end portion 94. A pair of bisecting diametrically opposed slots 96 are provided within the post 92 for receiving a pair of radially extending electrodes 98 and 100. The opposed slots 96 extend substantially the length of the post 92 and divide it into four equal parts. Each of the electrodes 98 and 100 have downwardly extending opposed legs 102 which extend into the opposed slots 96 and through the base portion 90a and are coupled together by soldering or the like so as to be connected to an electrical lead such as shown at 104.

After the electrical lead has been soldered to the legs 102, a recess portion 106 provided in the base member 90 is filled with any suitable epoxy cement. Integral with the upper end of the opposed leg 102 is a radially extending looped portion 110 so that the overall configuration of the two electrodes 98 and 100 is in the shape of an egg beater. The electrodes 98 and 100 are constructed of spring tempered beryllium copper wire which has a gold plate thereon. The resiliency of the electrodes 98 and 100 is sufficient to hold the plug 90 within the socket 88 of the shell 80. The diameter of the wire selected for the electrodes 98 and 100 dictates the force required for connecting and disconnecting the plug 90 from the shell 80. In one particular application, it is desired that this connecting and disconnecting force be approximately 6 to 8 ounces so as not to damage the implanted shell when coupling takes place.

While a preferred embodiment of the invention has been described using specific terms, such description is for illustrative purposes only, and it is to be understood that changes and variations may be made without departing from the spirit or scope of the following claims.

What is claimed is:

1. A percutaneous connector device for facilitating passage of electrical signals from an external source through the skin of a patient to internal portions of the body of said patient comprising:
    A. a shell constructed of electrically conductive material having an enlarged disk shaped base portion for being implanted below the skin of said patient
    B. a cylindrical portion having a first end portion integral with said enlarged disk shaped base portion and a second end portion extending outwardly therefrom for passing through the skin of said patient;
    C. a socket with a predetermined depth provided in and through said second end portion of said cylindrical portion to form an inner circular wall having a larger diameter adjacent said first end portion than adjacent said second end portion;
    D. plug means removably inserted in said socket for providing an electrical connection between said external source of electrical signals and said shell;
    E. said plug means including:
        i. a base portion,
        ii. a post attached to and extending outwardly from said base portion for a length substantially equal to said predetermined depth of said socket,
        iii. said post being provided with a pair of bisecting diametrically opposed slots extending substantially said length thereof and dividing said post into four equal parts,
        iv. a pair of radially extending electrodes carried by said plug means for making electrical contact with said shell,
        v. each of said pair of electrodes including conductive spring wire having an enlarged loop portion extending radially beyond said post and a pair of legs integral with said loop portion extending downwardly into one of said pair of bisecting diametrically opposed slots and terminating in end portions that extend through said base portion;
    F. means for coupling said electrical signals from said external source to said end portions of each said pair of legs that extend through said base portion; and,
    G. said enlarged loop portion of each of said pair of electrodes being resiliently biased radially outwardly for engaging said inner circular wall of said socket to produce a predetermined locking force between said shell and said plug means.

* * * * *